(12) United States Patent
Noda et al.

(10) Patent No.: US 6,977,506 B2
(45) Date of Patent: Dec. 20, 2005

(54) METHOD OF ANALYZING GAS USING QUARTZ OSCILLATOR AND APPARATUS THEREFOR

(75) Inventors: Kazutoshi Noda, Tsukuba (JP);
Ryuichi Naganawa, Tsukuba (JP);
Kunitoshi Matsunobu, Yokohama (JP);
Katsuhide Uchida, Hitachioota (JP);
Kouta Kobayashi, Atsugi (JP)

(73) Assignees: National Institute of Advanced Industrial Science and Technology, (JP); Gastec Corporation, (JP)

( * ) Notice: Subject to any disclaimer, the term of this patent is extended or adjusted under 35 U.S.C. 154(b) by 156 days.

(21) Appl. No.: 10/657,218

(22) Filed: Sep. 9, 2003

(65) Prior Publication Data
US 2004/0051535 A1    Mar. 18, 2004

(30) Foreign Application Priority Data
Sep. 18, 2002    (JP)    .............................. 2002-271189

(51) Int. Cl.$^7$ ....................... G01N 33/497; G01N 7/00; G01N 27/62
(52) U.S. Cl. ..................... 324/464; 73/19.01
(58) Field of Search ................. 324/464, 465, 324/674; 340/632, 634; 73/24.01, 24; 204/425

(56) References Cited

U.S. PATENT DOCUMENTS

| 5,411,709 A | * | 5/1995 | Furuki et al. | .................. 422/91 |
| 5,852,229 A | * | 12/1998 | Josse et al. | ................ 73/24.06 |
| 6,344,119 B2 | * | 2/2002 | Kato et al. | .................. 204/425 |

* cited by examiner

*Primary Examiner*—Anjan Deb
*Assistant Examiner*—John Teresinski
(74) *Attorney, Agent, or Firm*—Bacon & Thomas

(57) ABSTRACT

A gas analyzing apparatus including a reactor for decomposing a target substance contained in a gas to produce a product gas containing a decomposition product, a contacting chamber connected to the reactor and having a quartz oscillator disposed therewithin. The quartz oscillator has opposing surfaces each provided with an electrode, at least one of the electrodes being reactable with the decomposition product so that the decomposition product when contacted with the reactable electrode is reacted with the reactable electrode to cause a frequency deviation which is detected by a frequency measuring device.

3 Claims, 2 Drawing Sheets

METHOD OF ANALYZING GAS USING QUARTZ OSCILLATOR AND APPARATUS THEREFOR

CROSS-REFERENCE TO RELATED APPLICATIONS

This application claims, under 35 USC 119, priority of Japanese Application No. 2002-271189 filed Sep. 18, 2002.

BACKGROUND OF THE INVENTION

This invention relates to a method of quantitatively analyzing a target substance, such as a harmful substance, contained in a gas using a quartz oscillator and to an apparatus therefor.

Known gas analyzers include gas chromatographic gas analyzers, arc discharge ultraviolet spectroscopic gas analyzers and thermal ionization gas analyzers. These analyzers require high manufacturing costs.

A gas analyzer using a quartz oscillator as a sensor is also known (JP-A-H11-44625). The quartz oscillator has a lipid membrane capable of immobilizing a target substance contained in a gas. Upon absorption of the target substance, the oscillation frequency is changed due to an increase of the weight of the lipid membrane. Thus, by detecting the change in frequency of the quartz oscillator, it is possible to determine the concentration of the target substance in the gas. The conventional analyzer, however, has a problem because the sensitivity is not sufficiently high.

SUMMARY OF THE INVENTION

It is an object of the present invention to provide a method capable of quantitatively analyzing a trace amount of a target substance, such as a harmful substance, contained in a gas.

Another object of the present invention is to provide a simple, inexpensive apparatus which can analyze a trace amount of a target substance with high sensitivity.

It is a further object of the present invention to provide a small-sized apparatus which can measure in situ a target substance contained in a gas.

In accomplishing the above objects, there is provided in accordance with one aspect of the present invention a method of analyzing a concentration of a target substance contained in a gas, comprising the steps of:

(a) providing a quartz oscillator having opposing surfaces each provided with an electrode, at least one of said electrodes being reactable with said target substance;

(b) contacting said gas with said reactable electrode of said quartz oscillator so that the target substance is reacted with said reactable electrode; and (c) measuring a variation in frequency of said quartz oscillator in step (b).

In another aspect, the present invention provides a method of analyzing a concentration of a target substance contained in a gas, comprising the steps of:

(a) feeding said gas to a reactor to decompose said target substance and to produce a product gas containing a decomposition product;

(b) discharging said decomposition product gas from said reactor;

(c) providing a quartz oscillator having opposing surfaces each provided with an electrode, at least one of said electrodes being reactable with said decomposition product;

(d) contacting said discharged decomposition product gas from step (b) with said reactable electrode of said quartz oscillator so that said decomposition product is reacted with said reactable electrode; and (e) measuring a variation in frequency of said quartz oscillator in step (d).

The present invention also provides an apparatus for analyzing a concentration of a target substance contained in a gas, comprising:

a reactor configured to receive said gas and to decompose said target substance, thereby producing a product gas containing a decomposition product;

a contacting chamber;

a connecting passage extending between said reactor and said contacting chamber for discharging the product gas from said reactor and feeding same to said contacting chamber;

a quartz oscillator disposed in said contacting chamber and having opposing surfaces each provided with an electrode, at least one of said electrodes being reactable with said decomposition product so that said decomposition product is reacted with said reactable electrode when said product gas is contacted with said reactable electrode; and a device for measuring a variation in frequency of said quartz oscillator.

BRIEF DESCRIPTION OF THE DRAWINGS

Other objects, features and advantages of the present invention will become apparent from the detailed description of the preferred embodiments of the invention which follows, when considered in the light of the accompanying drawings, in which.

DETAILED DESCRIPTION OF THE PREFERRED EMBODIMENTS OF THE INVENTION

Figure 1:
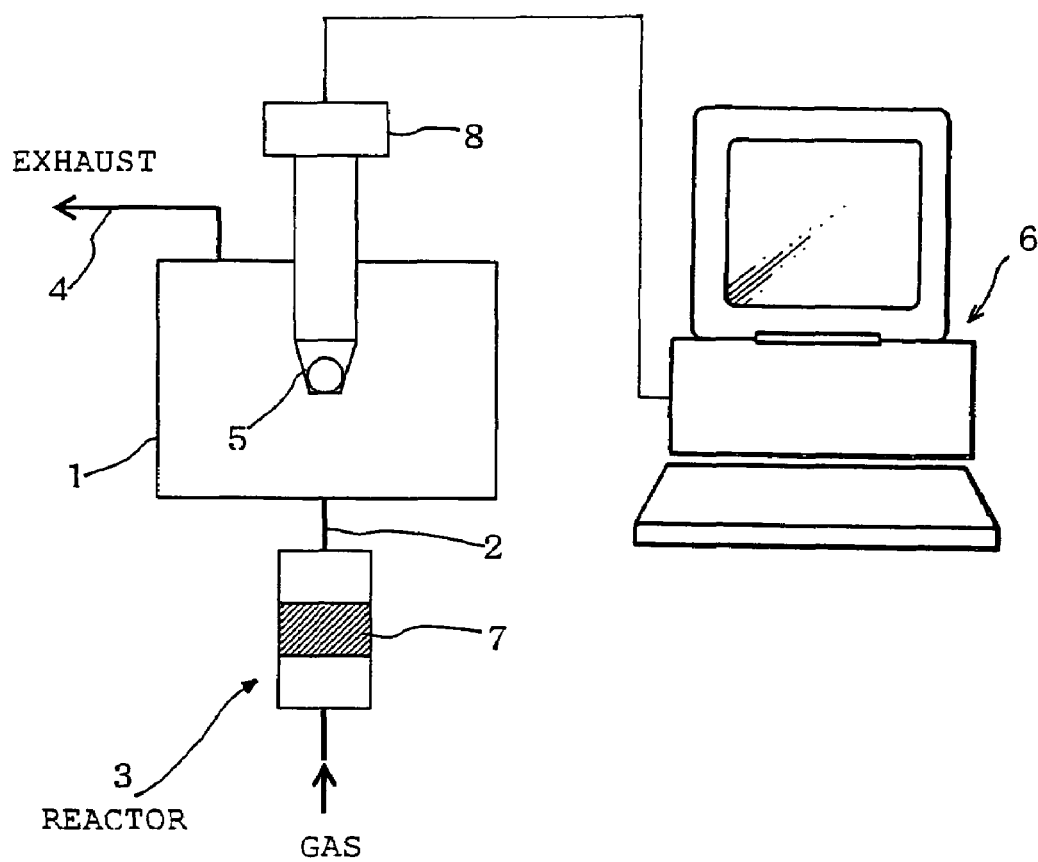
FIG. 1 is a schematic illustration of one embodiment of an apparatus for analyzing a concentration of a target substance contained in a gas in accordance with the present invention.

In the present invention, a quartz oscillator having opposing surfaces each provided with an electrode is used as a detector for detecting a target substance contained in a gas. At least one of the electrodes is reactable with the target substance. When the gas is contacted with the reactable electrode of the quartz oscillator, the target substance is reacted with the reactable electrode. The oscillation frequency of the quartz oscillator thus shifts as a result of a change in weight of the electrode caused by the reaction. By measuring the deviation or variation of the oscillation frequency, therefore, it is possible to determine the concentration of the target substance in the gas.

As used herein, the term "reaction" is intended to include chemical reaction, chemical corrosion and physical adsorption, which cause a change in weight of the electrode.

Any known quartz substrate may be used for the purpose of the invention. Electrodes are formed on front and rear surfaces of the crystal substrate by suitable known method such as sputtering. The electrodes are connected to a suitable known circuit capable of measuring a frequency deviation of the quartz oscillator. Generally, a quartz oscillator having a fundamental frequency of 12–100 MHz is used.

The reactable electrode is selected such that the target substance can react with the electrode. For example, a copper electrode is suitably used when the target substance is $H_2SO_4$ or HCl. A silver electrode is suitably used for a target substance of $Cl_2$ or $I_2$. Other metals or alloys such as aluminum and nickel may be used as the reactive electrode. Silver and copper are particularly preferred for reasons of high reactivity and, therefore, high sensitivity. The electrode is preferably maintained at a temperature in the range of 10–50° C.

When the target substance is not reactable with an electrically conductive metal electrode, it is first decomposed to produce a product gas containing a decomposition product reactable with the electrode. The decomposition product is then contacted with the electrode of the quartz oscillator for the reaction therewith to cause a frequency deviation.

The decomposition of the target substance may be carried out by any known method such as oxidation, reduction or photolysis. A catalyst may be used in the decomposition.

For example, when the target substance is a chloroorganic compound such as trichloroethylene, UV irradiation of the chloroorganic compound in the presence of a titanium oxide catalyst can decompose same to produce hydrogen chloride as a decomposition product.

When the target substance is an oxidizable substance such as an aromatic compound, e.g. benzene, toluene, xylene, chlorobenzene or o-dichlorobenzene; an aliphatic hydrocarbon, e.g. C5–C10 alkane; acetylene; or an oxidizable inorganic gas, e.g. carbon monoxide, the decomposition of the oxidizable substance may be preferably carried out by oxidizing the oxidizable substance with a first oxidizing agent of iodine pentoxide and a second oxidizing agent selected from the group consisting of sulfuric acid and pyrosulfuric acid to produce iodine as the decomposition product. In this case, the preferred reactable electrode is made of silver. The silver electrode is preferably maintained at a temperature in the range of 10–50° C.

The oxidation using the first and second oxidizing agents may be suitably carried out passing an oxidizable substance-containing gas through a packed bed of the first and second oxidizing agents. For this purpose, it is preferred that the first and second oxidizing agents be supported on a suitable carrier such as an inorganic metal oxide or a ceramic material. The carrier is preferably in the form of particles having a diameter of about 1–300 $\mu$m, preferably about 10–150 $\mu$m. Silica is suitably used. The amount of iodine pentoxide on the carrier is generally 0.05–0.5% by weight, preferably 0.1–0.4% by weight, based on the weight of the carrier. The amount of sulfuric acid or pyrosulfuric acid is generally 20–50% by weight, preferably 25–35% by weight, based on the weight of the carrier.

The oxidation may be carried out at any desired temperature, generally at −10° C. to 100° C., preferably 10–60° C., more preferably 20–30° C. The reaction pressure and relative humidity are not specifically limited. Ambient pressure is generally adopted. A relative humidity of 20–70% is suitably adopted.

When the target substance is a volatile chloroorganic compound such as trichloroethylene, tetrachloroethylene, 1,2-dichloroethylene or ethylene chloride, the decomposition of the chloroorganic compound may be preferably carried out by oxidizing the chloroorganic compound with lead oxide and sulfuric acid to produce hydrogen chloride as the decomposition product. In this case, the preferred reactable electrode is made of copper. The copper electrode is preferably maintained at a temperature in the range of 10–50° C.

The oxidation using lead oxide may be suitably carried out passing an oxidizable substance-containing gas through a packed bed of lead oxide and sulfuric acid. For this purpose, it is preferred that the lead oxide and sulfuric acid be supported on a suitable carrier such as an inorganic metal oxide or a ceramic material. The carrier is preferably in the form of particles having a diameter of about 1–300 $\mu$m, preferably about 10–150 $\mu$m. Silica is suitably used. The amount of lead oxide on the carrier is generally 0.5–2% by weight, preferably 0.8–1.2% by weight, based on the weight of the carrier. The amount of sulfuric acid is generally 2–7% by weight, preferably 3.5–5% by weight, based on the weight of the carrier.

The oxidation using lead oxide and sulfuric acid may be carried out at any desired temperature, generally at −10° C. to 100° C., preferably 10–60° C., more preferably 20–30° C. The reaction pressure and relative humidity are not specifically limited. Ambient pressure is generally adopted. A relative humidity of 20–70% is suitably adopted.

One preferred apparatus for analyzing a concentration of a target substance which is contained in a feed gas and which is not reactable with an electrically conductive metal electrode is illustrated in FIG. 1. The apparatus comprises a reactor 3 configured to receive the feed gas. The reactor 3 has a packed bed 7 of an oxidizing agent. Thus, when the feed gas is passed through the packed bed 7, the target substance contained therein is decomposed to produce a product gas containing a decomposition product.

Disposed downstream of and close to the reactor 3 is a contacting chamber 1 into which the product gas from the reactor 3 is introduced through a connecting passage 2 extending between the reactor 3 and the contacting chamber 1. Accommodated in the contacting chamber 1 is a quartz oscillator 5 having opposing surfaces each provided with an electrode (not shown).

At least one of the electrodes of the quartz oscillator 5 is reactable with the decomposition product contained in the product gas so that the product gas when contacted with the reactable electrode is reacted therewith. The quartz oscillator 5 has an output (indicative of a frequency) coupled to a detector (frequency measuring device) 8 and a controlling and processing unit 6 including a computer where the concentration of the target gas is calculated in the conventional manner from the frequency deviation detected by the frequency measuring device 8. The fundamental frequency of the quartz oscillator 5 is suitably determined in view of the desired sensitivity thereof. The output from the quartz oscillator 5 may be connected to the frequency measuring device 8 with or without wirings.

The product gas is discharged through a line 4 as an exhaust gas. The inside walls of the reactor 3, contacting chamber 1, gas flow passages 2 and 4 and other associated parts with which the decomposition product is contacted are suitably made of an inert material such as a polytetrafluoroethylene resin or a glass.

Each of the reactor 3 and the contacting chamber 1 is preferably provided with a temperature sensor whose output is electrically coupled to the controlling and processing unit 6. Since the decomposition efficiency of the target substance varies with the temperature in the reactor 3 and since the sensitivity (reactivity) of the electrode also varies with the temperature in the contacting chamber 1, the reactor 3 and the contacting chamber 1 are desired to be maintained at predetermined temperatures. The contacting chamber 3 is preferably constructed as a thermostatic chamber provided with suitable heaters and coolers.

The sensitivity of the quartz oscillator increases with an increase of the area of the reactable electrode. Thus, both electrodes can be made reactable and/or the area of the reactable electrode or electrodes can be increased, when a high sensitivity is desired. The amount of the oxidizing agent in the packed bed 7 and the flow rate of the gas feed containing the target substance also have an influence upon the amount of decomposition product in the product gas and, therefore, upon the sensitivity of the apparatus. Thus, suitable devices such as flow meters, pumps and temperature sensors may be preferably provided in the apparatus, although not shown in FIG. 1.

The concentration of the target substance may be determined from the measured frequency deviation using a previously prepared calibration curve obtained using a standard sample having a known concentration of the target substance under the same conditions.

The following example will further illustrate the present invention.

EXAMPLE 1

An analyzing apparatus as shown in FIG. 1 was prepared. A silver electrode was provided on each of the opposing sides of a quartz crystal substrate to prepare a quartz oscillator 5 having a fundamental frequency of 9 MHz.

Figure 2:
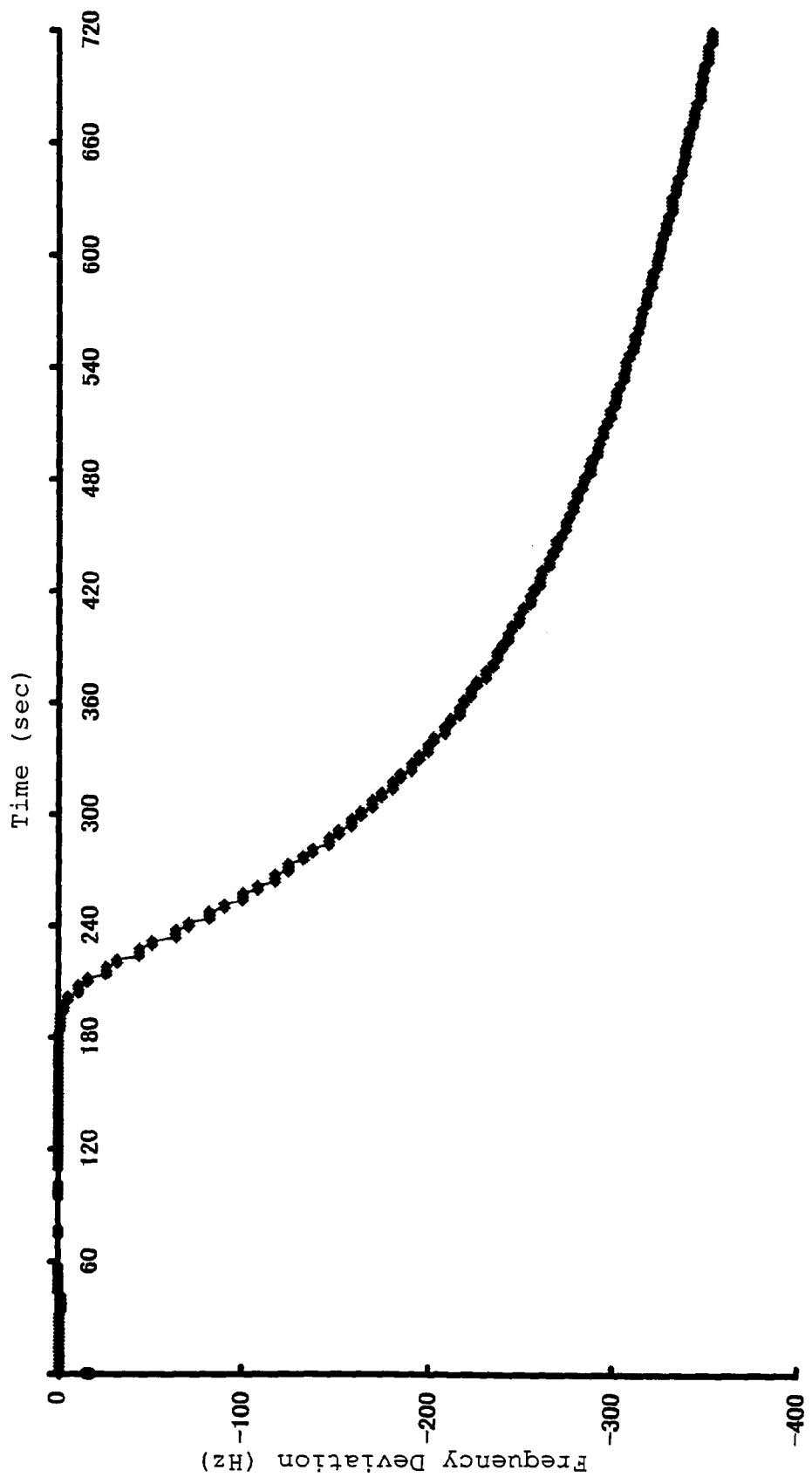
FIG. 2 is a graph showing a change of a frequency of a quartz oscillator caused by feeding benzene-containing gas.

The quartz oscillator 5 was then set in a contacting chamber 1 which was maintained at a constant temperature of 20° C. A glass tube having an inside diameter of 5 mm and a length of 80 mm was used as a reactor 3 and directly connected to the contacting chamber 1. In the reactor 3 was disposed a packed bed 7 containing 0.5 g of silica (particle size: about 100 $\mu$m) having supported thereon $I_2O_5$ and $H_2SO_4$. The reactor was maintained at 20° C. A dry nitrogen gas was passed through the reactor 3 and the contacting chamber at a flow rate of 100 ml/min for 3 minutes. Then, a nitrogen gas containing 100 ppb of benzene was fed to the reactor 3 at a flow rate of 100 ml/min for 9 minutes so that the benzene was oxidized with production of iodine. The product gas from the reactor 3 was immediately introduced into the contacting chamber 1 and discharged therefrom through a line 4. In the contacting chamber, the iodine was reacted with the silver electrodes. During the course of the gas feed, the frequency of the quartz oscillator 5 was measured in a frequency measuring device 8. The results of the measurement is shown in FIG. 2. A sensitivity of 1 ppb/Hz or higher was found to be attained.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

The teachings of Japanese Patent Application No. 2002-271189, filed Sep. 18, 2002, inclusive of the specification, claims and drawings, are hereby incorporated by reference herein.

What is claimed is:

1. A method of analyzing a concentration of a target substance contained in a gas, comprising the steps of:

(a) feeding said gas to a reactor to decompose said target substance and to produce a product gas containing a decomposition product;

(b) discharging said decomposition product gas from said reactor;

(c) providing a quartz oscillator having opposing surfaces each provided with an electrode, at least one of said electrodes being reactable with said decomposition product;

(d) contacting said discharged decomposition product gas from step (b) with said reactable electrode of said quartz oscillator so that said decomposition product is reacted with said reactable electrode; and (e) measuring a variation in frequency of said quartz oscillator in step (d); and wherein said target substance is an oxidizable substance selected from the group consisting of an aromatic compound, an aliphatic hydrocarbon, acetylene and an inorganic gas, wherein step (a) comprises oxidizing said oxidizable substance with iodine pentoxide and an oxidizing agent selected from the group consisting of sulfuric acid and pyrosulfuric acid to produce iodine as said decomposition product, and wherein said reactable electrode is made of silver.

2. An apparatus for analyzing a concentration of a target substance contained in a gas, comprising:

a reactor configured to receive said gas and to decompose said target substance, thereby producing a product gas containing a decomposition product, said reactor containing a packed bed of an oxidizing agent supported on silica carrier particles;

a contacting chamber;

a connecting passage extending between said reactor and said contacting chamber for discharging the product gas from said reactor and introducing same to said contacting chamber;

a quartz oscillator disposed in said contacting chamber and having opposing surfaces each provided with an electrode, at least one of said electrodes being reactable with said decomposition product so that said decomposition product is reacted with said reactable electrode when said product gas is contacted with said reactable electrode;

a device for measuring a frequency of said quartz oscillator; and wherein said oxidizing agent is reactable with the target substance to yield the decomposition product and is selected from a first combination of iodine pentoxide with sulfuric acid or pyrosulfuric acid, and a second combination of lead oxide with sulfuric acid, provided that said reactable electrode is silver when said oxidizing agent is said first combination and that said reactable electrode is copper when said oxidizing agent is said second combination.

3. A method of analyzing a concentration of a target substance contained in a gas, comprising the steps of:

(a) feeding said gas to a reactor to decompose said target substance and to produce a product gas containing a decomposition product;

(b) discharging said decomposition product gas from said reactor;

(c) providing a quartz oscillator having opposing surfaces each provided with an electrode, at least one of said electrodes being reactable with said decomposition product;

(d) contacting said discharged decomposition product gas from step (b) with said reactable electrode of said quartz oscillator so that said decomposition product is reacted with said reactable electrode; and (e) measuring a variation in frequency of said quartz oscillator in step (d); and wherein said target substance is a volatile chloroorganic compound, wherein step (a) comprises oxidizing said chloroorganic compound with lead oxide and sulfuric acid to produce hydrogen chloride as said decomposition product, and wherein said reactable electrode is made of copper.

* * * * *